US007141657B2

(12) United States Patent
Fujita et al.

(10) Patent No.: US 7,141,657 B2
(45) Date of Patent: Nov. 28, 2006

(54) AZO COMPOUND, TAUTOMER THEREOF, AND AZO DYE

(75) Inventors: Akinori Fujita, Shizuoka-ken (JP); Makoto Ohmoto, Shizuoka-ken (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/171,544

(22) Filed: Jul. 1, 2005

(65) Prior Publication Data

US 2006/0009627 A1    Jan. 12, 2006

(30) Foreign Application Priority Data

Jul. 7, 2004    (JP) .............................. 2004-200335

(51) Int. Cl.
*C09B 29/48*    (2006.01)
(52) U.S. Cl. ...................... 534/753; 534/769; 534/792; 8/692
(58) Field of Classification Search ................ 534/753, 534/769, 792; 8/692
See application file for complete search history.

(56) References Cited

U.S. PATENT DOCUMENTS

| 7,011,875 | B1 * | 3/2006 | Watanabe et al. | .......... | 428/64.1 |
| 2004/0213947 | A1 * | 10/2004 | Watanabe et al. | .......... | 428/64.4 |

FOREIGN PATENT DOCUMENTS

| JP | A 4-59287 | 2/1992 |
| JP | A 4-201483 | 7/1992 |
| JP | A 2003-221535 | 8/2003 |

OTHER PUBLICATIONS

J.Fabian and H. Hartmann, Light Absorption of Organic Colorants, Springer-Verlag, Berlin (1980).

Metwally et al., J. Indina Chem. Soc., vol. LXV, Jan. 1988, pp. 54-59.

Ernst Mohr., "87. About 1-phenyl-3-methyl-5-aminopyrazol[1] ", Journal fur Praktische Chemie [2] Bd. 79, 1909, 47.

* cited by examiner

*Primary Examiner*—Fiona T. Powers
(74) *Attorney, Agent, or Firm*—Margaret A. Burke; Sheldon J. Moss

(57) ABSTRACT

An azo compound or a tautomer thereof, wherein the azo compound is represented by the following Formula (1).

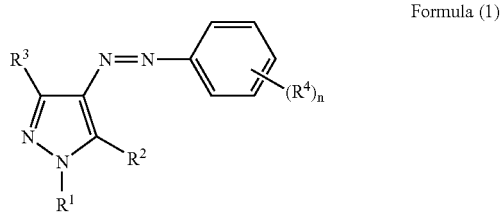

Formula (1)

In Formula (1), $R^1$ represents a hydrogen atom, alkyl group, aryl group, acyl group, carbamoyl group, alkylsulfonyl group, arylsulfonyl group, or heterocyclic group; $R^2$ represents —$NR^5R^6$ or —$OR^7$; $R^5$ and $R^6$ each independently represent a hydrogen atom, alkyl group, aryl group, acyl group, carbamoyl group, alkylsulfonyl group, or arylsulfonyl group; $R^7$ represents an alkyl group or aryl group; $R^3$ represents a hydrogen atom, alkyl group, aryl group, alkoxy group, aryloxy group, acylamino group, carbamoylamino group, alkylsulfonylamino group, or arylsulfonylamino group; n is an integer of 3 to 5; and each $R^4$, of which there are n in number, independently represents an alkyl group, aryl group, alkoxy group, aryloxy group, amino group, alkylthio group, arylthio group, acylamino group, alkylsulfonylamino group, or arylsulfonylamino group, and one $R^4$ may bind to another $R^4$ forming a ring.

8 Claims, No Drawings

AZO COMPOUND, TAUTOMER THEREOF, AND AZO DYE

CROSS-REFERENCE TO RELATED APPLICATION

This application claims priority under 35 USC 119 from Japanese Patent Application No. 2004-200335, the disclosure of which is incorporated by reference herein.

BACKGROUND OF THE INVENTION

1. Field of the Invention

The present invention relates to a new azo compound, a tautomer thereof and an azo dye, and in particular to a new azo compound, a tautomer thereof and an azo dye that are favorable in hue and superior in light fastness.

2. Description of the Related Art

Azo compounds have been used widely in various fields as dyes, because they absorb various visible lights different in wavelength, for example, as dyes for coloring synthetic resins, printing inks, sublimation-type heat-sensitive transfer materials, and inkjet-recording ink, and more recently, as functional dyes for use in the electronics field. Each azo compound has an absorption spectrum, which is a major property required for an azo compound as a dye. The hue of a dye exerts a significant influence on the hue, texture, and others of the material colored with the dye and a significant impact on visual impression. Accordingly the absorption spectra of dyes have long been studied, and reported in various literature (e.g., J. Fabian and H. Hartmann, "Light Absorption of Organic Colorants", Springer-Verlag, Berlin, 1980).

The properties needed for a dye vary significantly according to the applications thereof. Dyes having a favorable hue and dyeing efficiency are desirable for dyeing sheepskin or cowhide, while dyes having a favorable hue and being less water-soluble and thus being resistant to washing are favorable for use in apparels. Thus in many cases, dyes should have multiple functions that meet the specific demands required for a desired application. In addition, there exists a strong need for dyes favorable in hue and light fastness under various conditions for use in printing ink, dyes for sublimation-type heat-sensitive recording materials, or ink-jet-recording ink, and various diazo compounds or couplers have been disclosed for such purposes (e.g., Japanese Patent Application Laid-Open (JP-A) Nos. 4-59287 and 4-201483, and Mohr, J., J. Parkt. Chem., (2), 79, 1909, 47). However, although improvements have been made to some extent, there is still room for improvement in hue and light fastness.

SUMMARY OF THE INVENTION

The present invention, which has been made in view of the above circumstances, provides a new azo compound, a tautomer thereof and an azo dye that are favorable in hue and superior in light fastness.

A first aspect of the invention is to provide an azo compound or a tautomer thereof, wherein the as compound is represented by the following Formula (1):

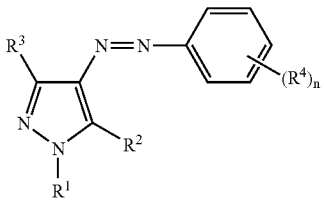

Formula (1)

wherein, $R^1$ represents a hydrogen atom, alkyl group, aryl group, acyl group, carbamoyl group, alkylsulfonyl group, arylsulfonyl group, or heterocyclic group; $R^2$ represents $-NR^5R^6$ or $-OR^7$; $R^5$ and $R^6$ each independently represent a hydrogen atom, alkyl group, aryl group, acyl group, carbamoyl group, alkylsulfonyl group or arylsulfonyl group; $R^7$ represents an alkyl group or aryl group; $R^3$ represents a hydrogen atom, alkyl group, aryl group, alkoxy group, aryloxy group, acylamino group, carbamoylamino group, alkylsulfonylamino group, or arylsulfonylamino group; n is an integer of 3 to 5; and each $R^4$, of which there are n in number, independently represents an alkyl group, aryl group, alkoxy group, aryloxy group, amino group, alkylthio group, arylthio group, acylamino group, alkylsulfonylamino group, or arylsulfonylamino group, and one $R^4$ may bind to another $R^4$ forming a ring.

A second aspect of the invention is to provide an azo dye represented by the following Formula (1).

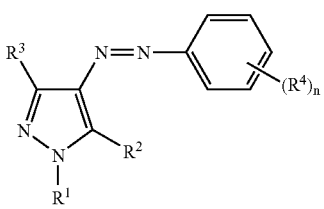

Formula (1)

wherein, $R^1$ represents a hydrogen atom, alkyl group, aryl group, acyl group, carbamoyl group, alkylsulfonyl group, arylsulfonyl group, or heterocyclic group; $R^2$ represents $-NR^5R^6$ or $-OR^7$; $R^5$ and $R^6$ each independently represent a hydrogen atom, alkyl group, aryl group, acyl group, carbamoyl group, alkylsulfonyl group or arylsulfonyl group; $R^7$ represents an alkyl group or aryl group; $R^3$ represents a hydrogen atom, alkyl group, aryl group, alkoxy group, aryloxy group, acylamino group, carbamoylamino group, alkylsulfonylamino group, or arylsulfonylamino group; n is an integer of 3 to 5; and each $R^4$, of which there are n in number, independently represents an alkyl group, aryl group, alkoxy group, aryloxy group, amino group, alkylthio group, arylthio group, acylamino group, alkylsulfonylamino group, or arylsulfonylamino group, and one $R^4$ may bind to another $R^4$ forming a ring.

DETAILED DESCRIPTION OF THE INVENTION

<Azo Compound>

The azo compound according to the present invention is represented by the following Formula (1).

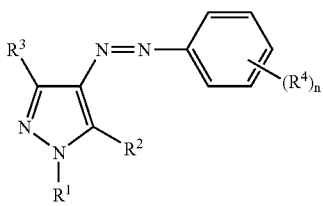

Formula (1)

In Formula (1), $R^1$ represents a hydrogen atom, alkyl group, aryl group, acyl group, carbamoyl group, alkylsulfonyl group, arylsulfonyl group, or heterocyclic group. $R^2$ represents —$NR^5R^6$ or —$OR^7$; $R^5$ and $R^6$ each independently represent a hydrogen atom, alkyl group, aryl group, acyl group, carbamoyl group, alkylsulfonyl group, or arylsulfonyl group; and $R^7$ represents an alkyl group or aryl group. $R^3$ represents a hydrogen atom, alkyl group, aryl group, alkoxy group, aryloxy group, acylamino group, carbamoylamino group, alkylsulfonylamino group, or arylsulfonylamino group. n is an integer of 3 to 5. Each $R^4$, of which there are n in number, independently represents an alkyl group, aryl group, alkoxy group, aryloxy group, amino group, alkylthio group, arylthio group, acylamino group, alkylsulfonylamino group, or arylsulfonylamino group; and one $R^4$ may bind to another $R^4$ forming a ring.

The azo compound according to the invention and tautomers thereof are useful as dyes that are favorable in hue and superior in light fastness. Tautomers of the azo compound are also included in the scope of the invention. The tautomers are the compounds that are present as the isomers of the azo compound represented by Formula (1), and the structure of the azo compound is easily interchangeable between these isomers.

In Formula (1), $R^2$ is particularly preferably —$NR^5R^6$. In such a case, among the azo compounds represented by Formula (1) and the tautomers thereof, the azo compounds represented by the following Formula (1-1) and the tautomers thereof are preferable.

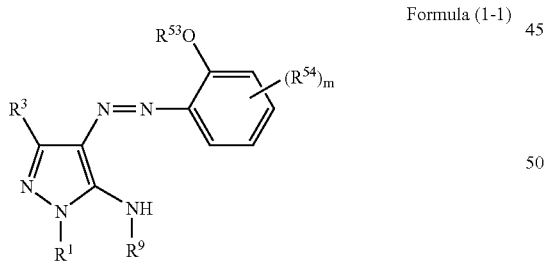

Formula (1-1)

In Formula (1-1), $R^1$ represents a hydrogen atom, alkyl group, aryl group, acyl group, carbamoyl group, alkylsulfonyl group, arylsulfonyl group, or heterocyclic group. $R^3$ represents a hydrogen atom, alkyl group, aryl group, alkoxy group, aryloxy group, acylamino group, carbamoylamino group, alkylsulfonylamino group, or arylsulfonylamino group. $R^9$ represents a hydrogen atom, alkyl group, aryl group, acyl group, carbamoyl group, alkylsulfonyl group, or arylsulfonyl group. $R^{53}$ represents an alkyl group or aryl group. m is an integer of 2 to 4. Each $R^{54}$, of which there are m in number, independently represents an alkyl group, aryl group, alkoxy group, aryloxy group, amino group, alkylthio group, arylthio group, acylamino group, alkylsulfonylamino group, or arylsulfonylamino group; and one $R^{54}$ may bind to another $R^{54}$ forming a ring.

In Formula (1), n is particularly preferably 3; and in Formula (1-1), m is particularly preferably 2.

Among the azo compounds represented by Formula (1) and the tautomers thereof, azo compounds represented by the following Formula (2) and the tautomers thereof are preferable:

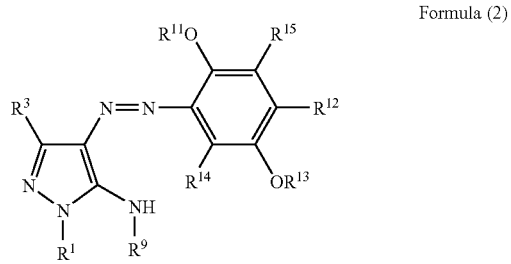

Formula (2)

In Formula (2), $R^1$ represents a hydrogen atom, alkyl group, aryl group, acyl group, carbamoyl group, alkylsulfonyl group, arylsulfonyl group, or heterocyclic group. $R^9$ represents a hydrogen atom, alkyl group, aryl group, acyl group, carbamoyl group, alkylsulfonyl group, or arylsulfonyl group. $R^3$ represents a hydrogen atom, alkyl group, aryl group, alkoxy group, aryloxy group, acylamino group, carbamoylamino group, alkylsulfonylamino group, or arylsulfonylamino group. $R^{11}$ and $R^{13}$ each independently represent an alkyl group or aryl group. $R^{12}$ represents an alkoxy group, aryloxy group, amino group, alkylthio group, arylthio group, acylamino group, alkylsulfonylamino group, or arylsulfonylamino group. $R^{14}$ and $R^{15}$ each independently represent a hydrogen atom, alkyl group, alkoxy group, or aryloxy group.

Further, among the azo compounds represented by Formula (1) and the tautomers thereof, azo compounds represented by the following Formula (3) and the tautomers thereof are preferable:

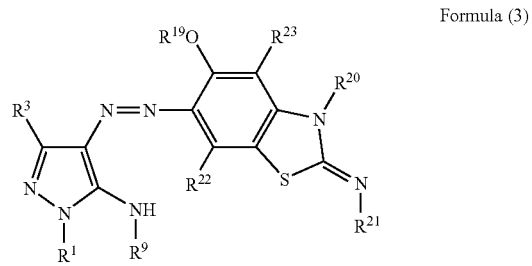

Formula (3)

In Formula (3), $R^1$ represents a hydrogen atom, alkyl group, aryl group, acyl group, carbamoyl group, alkylsulfonyl group, arylsulfonyl group, or heterocyclic group. $R^9$ represents a hydrogen atom, alkyl group, aryl group, acyl group, carbamoyl group, alkylsulfonyl group, or arylsulfonyl group. $R^3$ represents a hydrogen atom, alkyl group, aryl group, alkoxy group, aryloxy group, acylamino group, carbamoylamino group, alkylsulfonylamino group, or arylsulfonylamino group. $R^{19}$ represents an alkyl group or aryl group. $R^{20}$ represents a hydrogen atom, alkyl group, or aryl group. $R^{21}$ represents a hydrogen atom, alkyl group, aryl group, acyl group, alkylsulfonyl group, arylsulfonyl group, or carbamoyl group. $R^{22}$ and $R^{23}$ each independently represent a hydrogen atom, alkyl group, or aryl group.

The alkyl group in Formula (1), (1-1), (2), or (3) is preferably an alkyl group having 1 to 25 carbon atoms, and more preferably an alkyl group having 4 to 18 carbon atoms. The alkyl group may have a substituent group, and preferable examples of the substituent groups include halogen atoms, alkoxy groups, aryloxy groups, aryl groups, alkoxycarbonyl groups, acyloxy groups, carbamoyl groups, a cyano group, a carboxylic acid group, a sulfonic acid group and heterocyclic rings. Preferable examples of the (substituted) alkyl groups include methyl, ethyl, n-propyl, isopropyl, n-butyl, isobutyl, t-butyl, n-pentyl, isopentyl, n-hexyl, n-octyl, 2-ethylhexyl, t-octyl, n-decyl, n-dodecyl, n-octadecyl, trichloromethyl, benzyl, phenylethyl, ethoxyethyl, phenoxyethyl, methoxycarbonylpropyl, acetyloxyethyl, N-butylcarbamoylethyl, acetylaminoethyl, 2-cyano butyl, and furfuryl groups; methyl, ethyl, n-propyl, isopropyl, n-butyl, isobutyl, t-butyl, n-hexyl, n-octyl, 2-ethylhexyl, t-octyl, benzyl, and phenylethyl groups are more preferable; and methyl, ethyl, n-propyl, n-butyl, t-butyl, n-hexyl, and benzyl groups are particularly preferable.

The aryl group in Formula (1), (1-1), (2), or (3) is preferably an aryl group having 6 to 30 carbon atoms, and more preferably an aryl group having 6 to 20 carbon atoms. The aryl group may have a substituent group, and preferable examples the substituent group include halogen atoms, alkyl groups, aryl groups, alkoxy groups, aryloxy groups, alkylthio groups, arylthio groups, alkoxycarbonyl groups, aryloxycarbonyl groups, acyloxy groups, carbamoyl groups, alkoxycarbonylamino groups, aryloxycarbonylamino groups, carbamoylamino groups, alkoxycarbonyl groups, amino groups, a cyano group, and a nitro group. Preferable examples of the (substituted) aryl group include phenyl, naphthyl, 2-methoxyphenyl, 2-decyloxyphenyl, 4-methoxyphenyl, 2-octyloxynaphthyl, dimethylaminophenyl, 2-dodecylthiophenyl, 4-methylphenylthiophenyl, 2,5-dioctyloxyphenyl, 2-methoxy-4-dodecylthiophenyl, 2,5-dibenzyloxyphenyl, 2-methoxy-4benzyloxycarbonylaminophenyl, 2butoxy-4-acylaminophenyl, and 2,6-dioctyloxyphenyl groups; and phenyl, naphthyl, 2-methoxyphenyl, 2-decyloxyphenyl, 4-methoxyphenyl, 2-octyloxynaphthyl, dimethylaminophenyl, 2-methoxy-4-dodecylthiophenyl, 2,5benzyloxyphenyl, 2-methoxy-4-benzyloxycarbonylaminophenyl, 2-butoxy-4-acylaminophenyl, and 2,6-dioctyloxyphenyl groups are more preferable.

The acyl group in Formula (1), (1-1), (2), or (3) is preferably an acyl group having 1 to 20 carbon atoms, and more preferably an acyl group having 2 to 18 carbon atoms. The acyl group may have a substituent group, and preferable examples the substituent group include halogen atoms, alkoxy groups, aryloxy groups, a cyano group, and a nitro group. Preferable examples of the (substituted) acyl groups include ethanoyl, propanoyl, butanoyl, haxanoyl, 2-ethylhaxanoyl, octanoyl, decanoyl, benzoyl, 2-naphthoyl, butoxyethanoyl, trichloroethanoyl, 4-chlorobenzoyl, 4-nitrobenzoyl, 4-phenoxybenzoyl, and 4-cyanobenzoyl groups; ethanoyl, propanoyl, butanoyl, haxanoyl, 2-ethylhaxanoyl, octanoyl, decanoyl, benzoyl, 4-chlorobenzoyl, and 4-nitrobenzoyl groups are more preferable; and ethanoyl, propanoyl, butanoyl, haxanoyl, 2-ethylhaxanoyl, and benzoyl groups are particularly preferable.

The carbamoyl group in Formula (1), (1-1), (2), or (3) is preferably a carbamoyl group having 1 to 20 carbon atoms, and more preferably a carbamoyl group having 1 to 18 carbon atoms. The carbamoyl group may have a substituent group, and preferable examples the substituent groups include halogen atoms, alkoxy groups, aryloxy groups, a cyano group, and a nitro group. Examples of the (substituted) carbamoyl group include dimethylcarbamoyl, ethylcarbamoyl, dibutylcarbamoyl, cyclohexylcarbamoyl, phenylcarbamoyl, 2-ethylhexylcarbamoyl, decylcarbamoyl, methylethylcarbamoyl, benzylcarbamoyl, methoxyethylcarbamoyl, naphthylcarbamoyl, 4-cyanophenylcarbamoyl, and 4-nitrophenylcarbamoyl groups; dimethylcarbamoyl, ethylcarbamoyl, dibutylcarbamoyl, cyclohexylcarbamoyl, phenylcarbamoyl, 2-ethylhexylcarbamoyl, decylcarbamoyl, methylethylcarbamoyl, benzylcarbamoyl, methoxyethylcarbamoyl, and naphthylcarbamoyl groups are more preferable; and dimethylcarbamoyl, ethylcarbamoyl, dibutylcarbamoyl, cyclohexylcarbamoyl, phenylcarbamoyl, 2-ethylhexylcarbamoyl, and decylcarbamoyl groups are particularly preferable.

The alkylsulfonyl group in Formula (1), (1-1), (2), or (3) is preferably an alkylsulfonyl group having 1 to 20 carbon atoms, and more preferably an alkylsulfonyl group having 1 to 18 carbon atoms. The alkylsulfonyl group may have a substituent group, and preferable examples the substituent groups include halogen atoms, aryl groups, alkoxy groups, aryloxy groups, alkoxycarbonyl groups, acyloxy groups, carbamoyl groups, a cyano group, a carboxylic acid group, a sulfonic acid group, and heterocyclic rings. Preferable examples of the (substituted) alkylsulfonyl groups include methylsulfonyl, ethylsulfonyl, n-butylsulfonyl, n-octylsulfonyl, n-decylsulfonyl, dodecylsulfonyl, phenylmethylsulfonyl, trichloromethylsulfonyl, ethoxyethylsulfonyl, and phenoxyethylsulfonyl groups; methylsulfonyl, n-butylsulfonyl, n-octylsulfonyl, phenylmethylsulfonyl, and trichloromethylsulfonyl groups are more preferable; and methylsulfonyl, n-octylsulfonyl, and trichloromethylsulfonyl groups are particularly preferable.

The arylsulfonyl group in Formula (1), (1-1), (2), or (3) is preferably an arylsulfonyl group having 6 to 20 carbon atoms, and more preferably an arylsulfonyl group having 6 to 12 carbon atoms. The arylsulfonyl group may have a substituent group, and preferable examples the substituent groups include halogen atoms, alkyl groups, aryl groups, alkoxy groups, aryloxy groups, alkoxycarbonyl groups, acyloxy groups, carbamoyl groups, a cyano group, a carboxylic acid group, a sulfonic acid group, and heterocyclic rings. Preferable examples of the (substituted) arylsulfonyl group include phenylsulfonyl, toluenesulfonyl, chlorobenzenesulfonyl, 4butoxybenzenesulfonyl, dichlorobenzenesulfonyl, naphthylsulfonyl, dimethylaminobenzenesulfonyl, and ethoxycarbonylbenzenesulfonyl groups; phenylsulfonyl, toluenesulfonyl, chlorobenzenesulfonyl, and 4-butoxybenzenesulfonyl groups are more preferable; and phenylsulfonyl, toluenesulfonyl, and chlorobenzenesulfonyl groups are particularly preferable.

The heterocyclic group in Formula (1), (1-1), (2), or (3) is preferably a five- or six-membered ring, either aromatic or non-aromatic. The heterocyclic group may be a fused ring. Specific examples thereof include pyrrole, furan, pyridine, pyrimidine, triazine, thiazole, oxazole, benzthiazole, benzoxazole, piperidine, and pyran rings. The heterocyclic ring may have a substituent group, and preferable examples of the substituent groups include alkoxy groups, aryloxy groups, acylamino groups, alkylamino groups, arylamino groups, alkylsulfonylamino groups, arylsulfonylamino groups, a cyano group, a nitro group, and halogen atoms.

The alkoxy group in Formula (1), (1-1), (2), or (3) is preferably an alkoxy group having 1 to 20 carbon atoms, and more preferably an alkoxy group having 1 to 18 carbon atoms. The alkoxy group may have a substituent group, and preferable examples the substituent groups include halogen atoms, aryl groups, alkoxy groups, aryloxy groups, alkylthio groups, arylthio groups, a cyano group, and a nitro group. Preferable examples of the (substituted) alkoxy group include methyloxy, ethyloxy, n-propyloxy, isopropyloxy, n-butyloxy, isobutyloxy, t-butyloxy, hexyloxy, 2-ethylhexyloxy, octyloxy, decyloxy, benzyloxy, phenethyloxy, phenoxyethoxy, dodecyltioxyethyloxy, naphthoxyethoxy, 4-methylphenylthioethoxy, cyanomethoxy, and trichloromethoxy groups; methyloxy, ethyloxy, n-propyloxy, isopropyloxy, n-butyloxy, isobutyloxy, t-butyloxy, hexyloxy, 2-ethylhexyloxy, octyloxy, decyloxy, benzyloxy, phenethyloxy, and phenoxyethoxy groups are more preferable; and methyloxy, ethyloxy, isopropyloxy, t-butyloxy, hexyloxy, 2-ethylhexyloxy, octyloxy, decyloxy, benzyloxy, phenethyloxy, and phenoxyethoxy groups are particularly preferable.

The aryloxy group in Formula (1), (1-1), (2), or (3) is preferably an aryloxy group having 6 to 20 carbon atoms, and more preferably an aryloxy group having 6 to 12 carbon atoms. The aryloxy group may have a substituent group, and preferable examples the substituent groups include halogen atoms, alkyl groups, aryl groups, alkoxy groups, aryloxy groups, alkylthio groups, arylthio groups, a cyano group, and a nitro group. Preferable examples of the (substituted) aryloxy group include phenoxy, 4-methylphenyloxy, 3-methylphenyloxy, 2-methylphenyloxy, 4-chlorophenyloxy, 2-chlorophenyloxy, 4-methoxyphenyloxy, 4-phenoxyphenyloxy, 4-dodecyltioxyphenyloxy, and 4-cyanophenyloxy groups; phenoxy, 4-methylphenyloxy, 3-methylphenyloxy, 2-methylphenyloxy, 4-chlorophenyloxy, 2-chlorophenyloxy, 4-methoxyphenyloxy, and 4-phenoxyphenyloxy groups are more preferable; and phenoxy, 4-methylphenyloxy, 4-chlorophenyloxy, 4-methoxyphenyloxy groups are particularly preferable.

The acylamino group in Formula (1), (1-1), (2), or (3) is preferably an acylamino group having 1 to 20 carbon atoms, and more preferably an acylamino group having 1 to 12 carbon atoms. The acylamino group may have a substituent group, and preferable examples of the substituent groups include halogen atoms, alkoxy groups, aryloxy groups, a cyano group, and a nitro group. Preferable examples of the (substituted) acylamino group include ethanoylamino, butanoylamino, 2-ethylhaxanoylamino, benzoylamino, decanoylamino, ethoxyethanoylamino, 4-nitrobenzoylamino, 2-methoxybenzoylamino, and phenoxybutanoylamino groups; ethanoylamino, butanoylamino, 2-ethylhaxanoylamino, benzoylamino, decanoylamino, and ethoxyethanoylamino groups are more preferable; and ethanoylamino, butanoylamino, 2-ethylhaxanoylamino, benzoylamino, and decanoylamino groups are particularly preferable.

The carbamoylamino group in Formula (1), (1-1), (2), or (3) is preferably a carbamoylamino group having 1 to 20 carbon atoms, and more preferably a carbamoylamino group having 1 to 12 carbon atoms. The carbamoylamino group may have a substituent group, and preferable examples the substituent groups include halogen atoms, alkoxy groups, aryloxy groups, a cyano group, and a nitro group. Preferable examples of the (substituted) carbamoylamino group include N,N-dimethylcarbamoylamino, N-phenylcarbamoylamino, N-cyclohexylcarbamoylamino, N-butylcarbamoylamino, N-benzylcarbamoylamino, N,N-diethylcarbamoylamino, and N-hexylcarbamoylamino groups; and N-phenylcarbamoylamino, N-cyclohexylcarbamoylamino, N-butylcarbamoylamino, and N-benzylcarbamoylamino groups are more preferable.

The alkylsulfonylamino group in Formula (1), (1-1), (2), or (3) is preferably an alkylsulfonylamino group having 1 to 20 carbon atoms, and more preferably an alkylsulfonylamino group having 1 to 12 carbon atoms. The alkylsulfonylamino group may have a substituent group, and preferable examples the substituent groups include halogen atoms, alkoxy groups, aryloxy groups, a cyano group, and a nitro group. Preferable examples of the (substituted) alkylsulfonylamino groups include methylsulfonylamino, ethylsulfonylamino, butylsulfonylamino, octylsulfonylamino, decylsulfonylamino, benzylsulfonylamino, chloroethylsulfonylamino, and phenoxyethylsulfonylamino groups; methylsulfonylamino, ethylsulfonylamino, butylsulfonylamino, octylsulfonylamino, decylsulfonylamino, benzylsulfonylamino, and chloroethylsulfonylamino groups are more preferable; and methylsulfonylamino, ethylsulfonylamino, butylsulfonylamino, octylsulfonylamino, decylsulfonylamino, and benzylsulfonylamino groups are particularly preferable.

The arylsulfonylamino group in Formula (1), (1-1), (2), or (3) is preferably an arylsulfonylamino group having 6 to 20 carbon atoms, and more preferably an arylsulfonylamino group having 6 to 12 carbon atoms. The arylsulfonylamino group may have a substituent group, and preferable examples the substituent groups include halogen atoms, alkoxy groups, aryloxy groups, a cyano group, and a nitro group. Preferable examples of the (substituted) arylsulfonylamino groups include phenylsulfonylamino, 4-methylphenylsulfonylamino, naphthylsulfonylamino, 4-methoxyphenylsulfonylamino, N-methylphenylsulfonylamino, and 4-cyanophenylsulfonylamino groups; phenylsulfonylamino, 4-methylphenylsulfonylamino, and naphthylsulfonylamino groups are more preferable; and phenylsulfonylamino and 4-methylphenylsulfonylamino groups are particularly preferable.

The amino group in Formula (1), (1-1), (2), or (3) is preferably an amino group having 0 to 20 carbon atoms, and more preferably an amino group having 0 to 16 carbon atoms. The amino group may have a substituent group, and preferable examples the substituent groups include alkyl groups and aryl groups. Preferable examples of the (substituted) amino groups include amino, N-methylamino, N,N-dimethylamino, N,N-dioctylamino, N-phenylamino, N,N-diphenylamino, N-phenyl-N-methylamino, N,N-dimethoxyethylamino, N-benzylamino, N,N-dibenzylamino, N,N-diisopropylamino, and piperidine groups; amino, N-methylamino, N,N-dimethylamino, N,N-ioctylamino, N-phenylamino, N-phenyl-N-methylamino, N-benzylamino, N,N-dibenzylamino, and N,N-diisopropylamino groups are more preferable; and amino, N-methylamino, N,N-dimethylamino, N,N-dioctylamino, N-benzylamino, N,N-dibenzylamino, and N,N-diisopropylamino groups are particularly preferable.

The alkylthio group in Formula (1), (1-1), (2), or (3) is preferably an alkylthio group having 1 to 20 carbon atoms, and more preferably an alkylthio group having 1 to 18 carbon atoms. The alkylthio group may have a substituent group, and preferable examples the substituent groups include halogen atoms, alkyl groups, aryl groups, alkoxy groups, aryloxy groups, alkylthio groups, arylthio groups, a cyano group, and a nitro group. Preferable examples of the (substituted) alkylthio group include methylthio, ethylthio, n-butylthio, n-hexylthio, n-decylthio, n-dodecylthio, benzylthio, n-octadecylthio, methoxyethylthio, and chloropropylthio groups; and methylthio, ethylthio, n-butylthio, n-hexylthio, n-decylthio, n-dodecylthio, and benzylthio groups are particularly preferable.

The arylthio group in Formula (1), (1-1), (2), or (3) is preferably an arylthio group having 6 to 20 carbon atoms, and more preferably an arylthio group having 6 to 12 carbon atoms is more preferable as. The arylthio group may have a substituent group, and preferable examples the substituent groups include halogen atoms, alkyl groups, aryl groups, alkoxy groups, aryloxy groups, alkylthio groups, arylthio groups, a cyano group, and a nitro group. Preferable examples of the (substituted) arylthio group include phenylthio, tolylthio, naphthylthio, 4-butoxyphenylthio, and 4-phenoxyphenylthio groups.

Specific examples of the azo compounds according to the invention (A-1 to A-40) will be listed below; but the invention is not restricted by the following compounds. In addition, tautomers of the following specific examples are also included in the scope of the invention. In the specific examples (A-1 to A-40), Ph represents a phenyl group; Me, a methyl group; Et, an ethyl group; and Ac, an acetyl group.

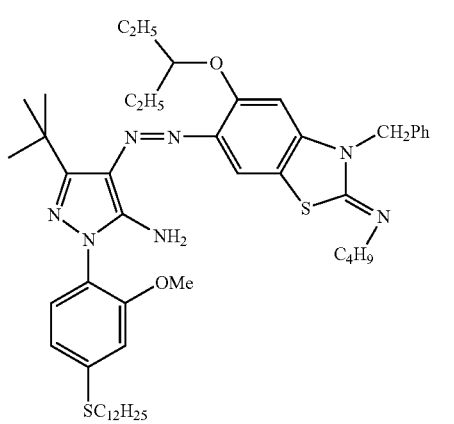
(A-1)

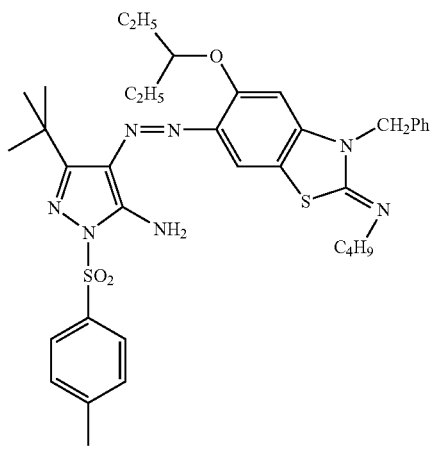
(A-2)

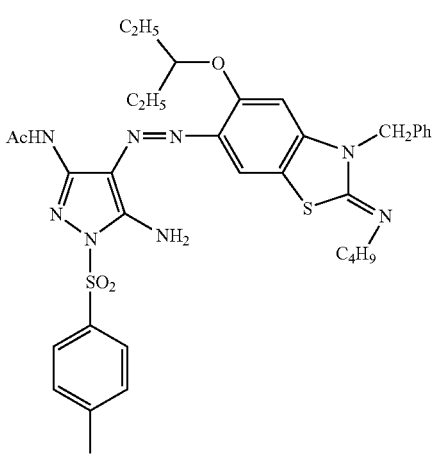
(A-3)

-continued

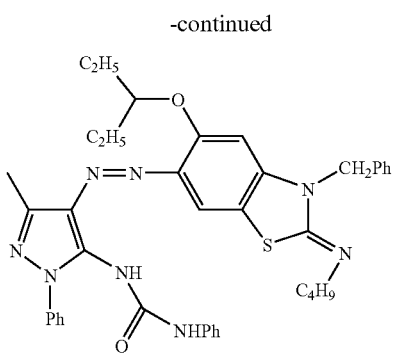
(A-4)

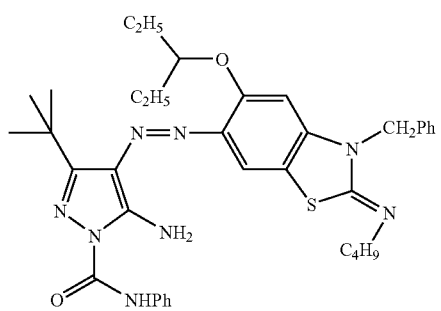
(A-5)

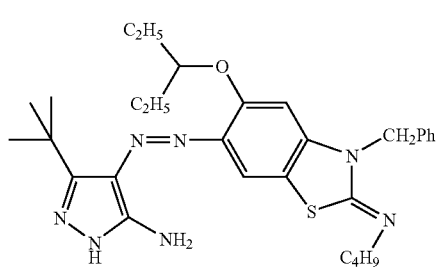
(A-6)

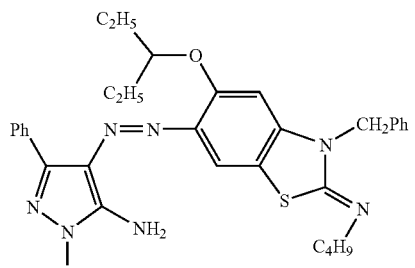
(A-7)

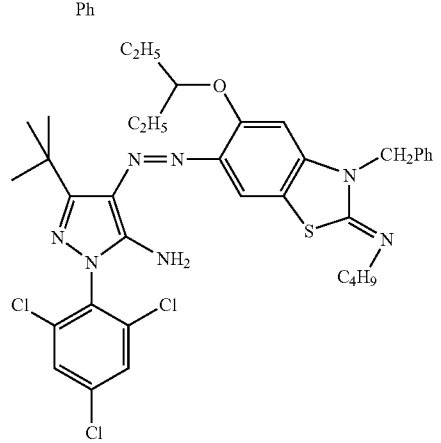
(A-8)

-continued
(A-9)
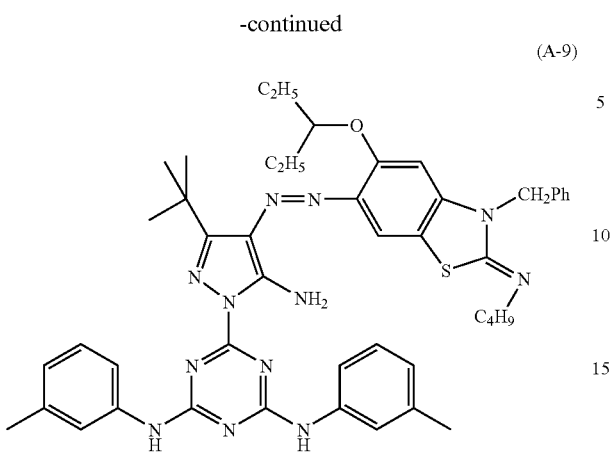
(A-13)
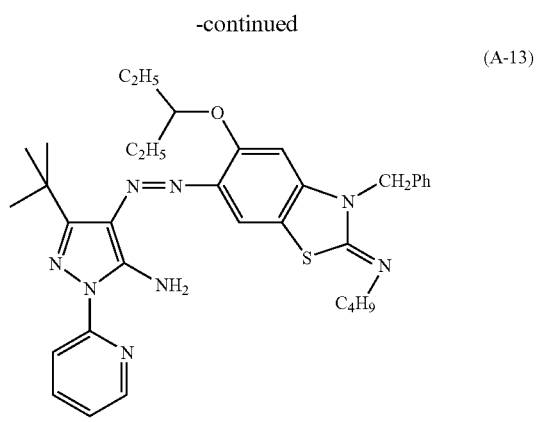
(A-10)
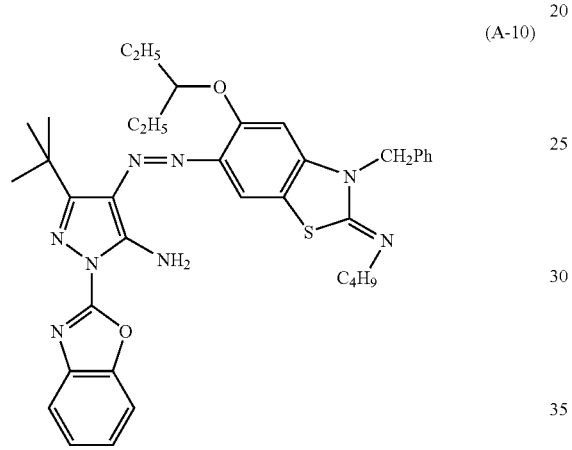
(A-14)
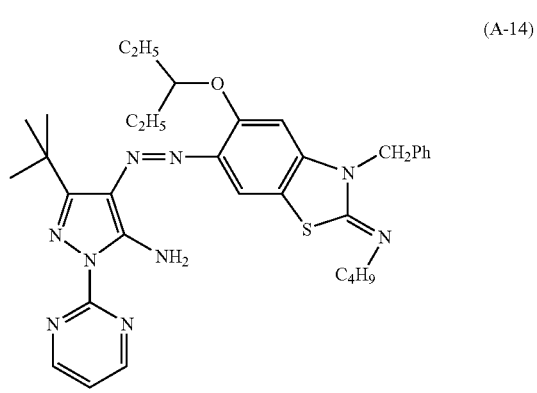
(A-11)
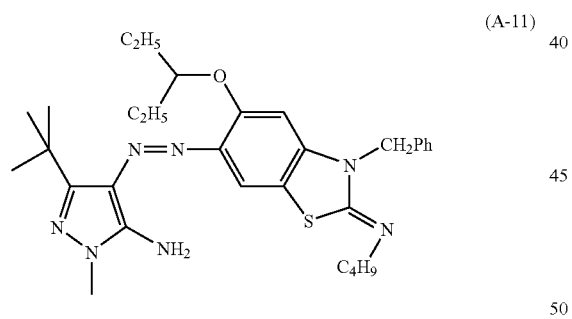
(A-15)
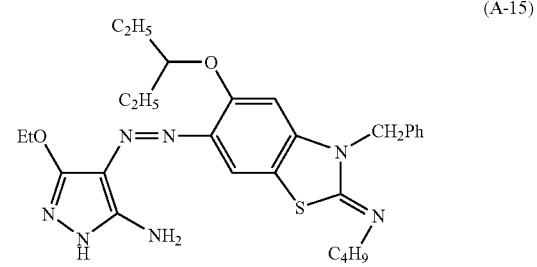
(A-12)
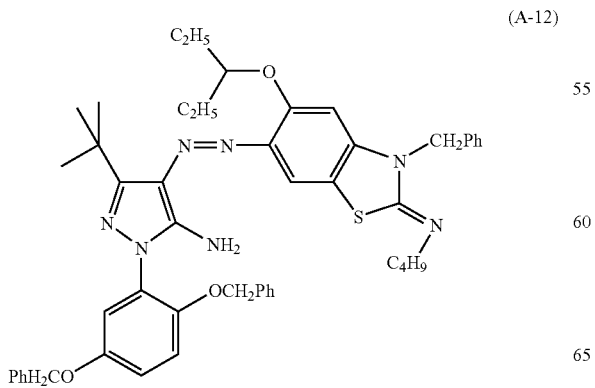
(A-16)
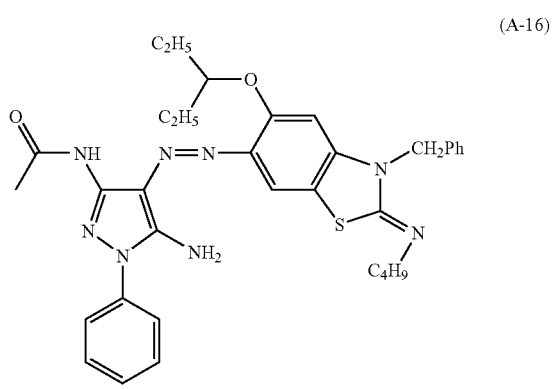

-continued (A-17)
(A-18)
(A-19)
(A-20)
(A-21)
(A-22)
(A-23)
(A-24)
(A-25)

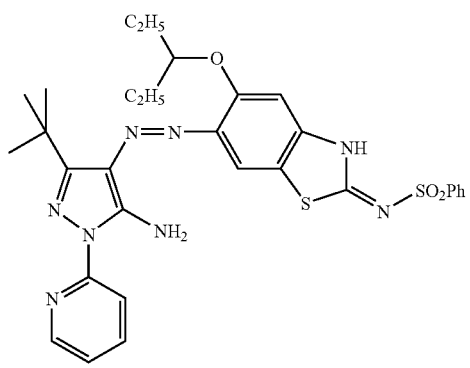
(A-26)
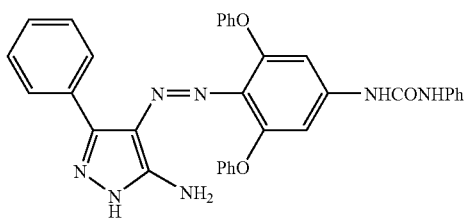
(A-30)
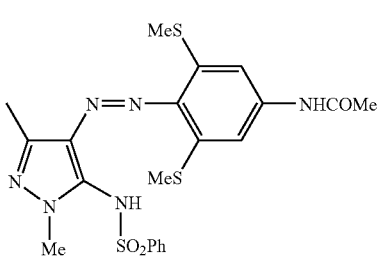
(A-31)
(A-27)
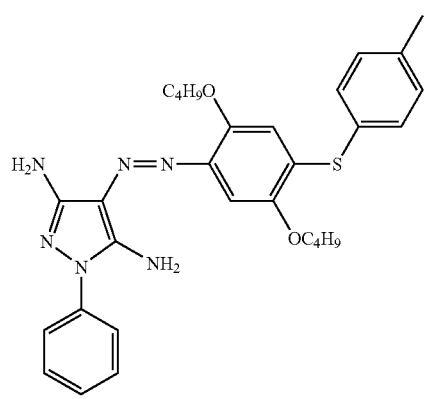
(A-32)
(A-28)
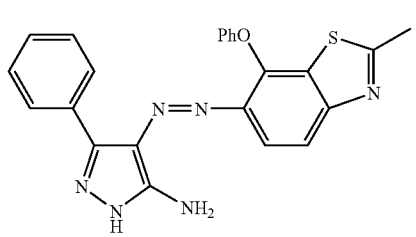
(A-33)
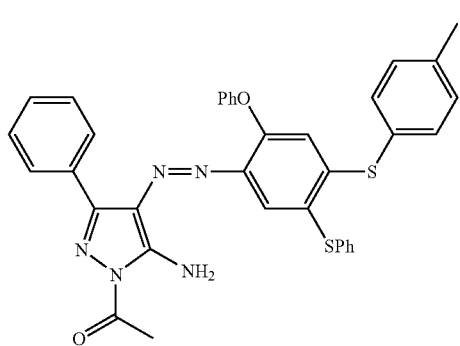
(A-29)
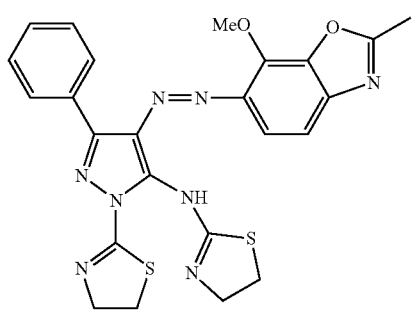
(A-34)

-continued

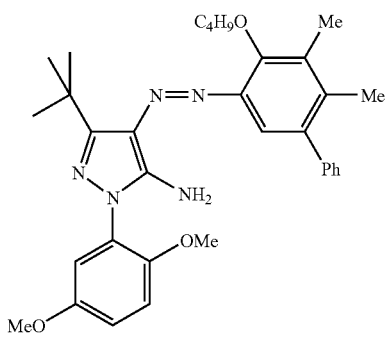
(A-35)

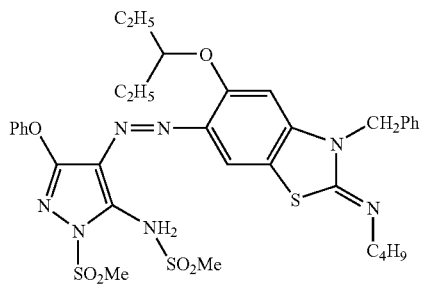
(A-36)

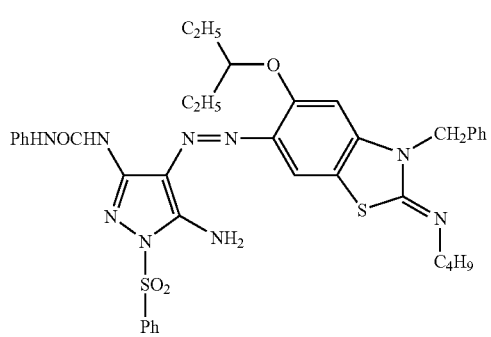
(A-37)

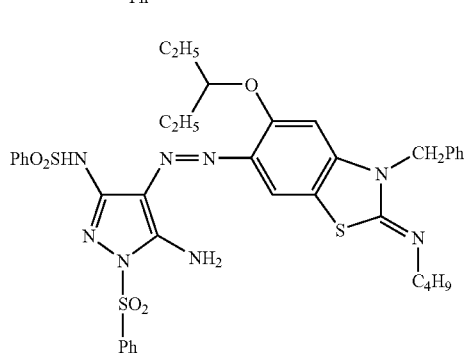
(A-38)

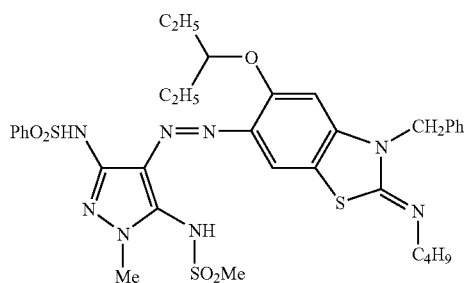
(A-39)

-continued

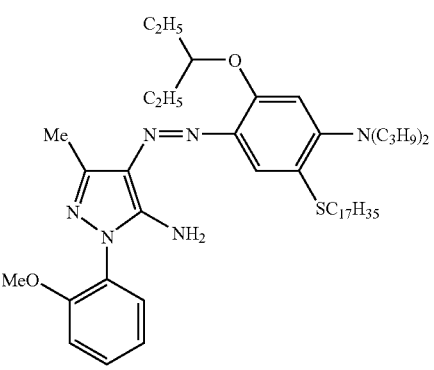
(A-40)

<Method for Producing Azo Compound>

The method for producing the azo compound according to the invention will be described below. Various synthetic methods for azo compounds have been reported, for example, in H. Zollinger, "Color Chemistry", 1991, Weinheim, p. 109 and others. Among them, the method of producing azo compounds by the reaction of a diazonium salt and a coupler compound is useful as it is widely used. The azo compounds according to the invention may also be produced in the reaction of a diazonium salt and a coupler compound.

An azo compound according to the invention represented by Formula (1) can be synthesized by the reaction of a diazonium salt represented by the following Formula (a) and a pyrazole compound represented by the following Formula (b).

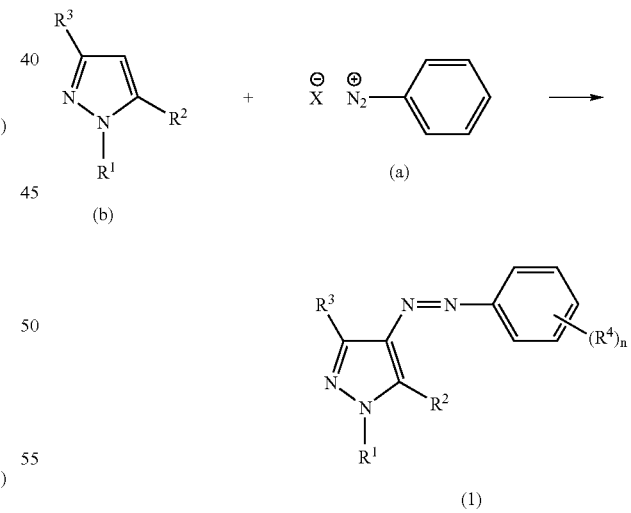

In Formulae (a) and (b), $R^1$, $R^2$, $R^3$, and $R^4$ are the groups same as $R^1$, $R^2$, $R^3$, and $R^4$ in Formula (1). X represents a counter anion such as a chloride ion, $BF_4^-$, or $PF_6^-$. Various solvents may be used as the solvent, and examples thereof include water, alcohol, ethyl acetate, ether, THF, and the like. An organic or inorganic base may also be added for the purpose of increasing the yield. Examples of the bases include sodium hydroxide, ammonia, triethylamine, pyridine, sodium bicarbonate, and the like.

19

<Azo Dye>

The azo dye according to the invention is an azo compound according to the invention above, namely, the azo compound represented by any one of Formulae (1), (1-1), (2), and (3). Thus, the azo dye according to the invention is a dye that is favorable in hue and superior in light fastness, similarly to the azo compound according to the invention described above.

EXAMPLES

Example 1

<Synthesis of Compound (A-1)>

The following coupler A (5 g) was dissolved in methanol (50 ml), and then diazonium salt A (5.5 g) was added thereto. 100 ml of water and 100 ml of ethyl acetate were added to the reaction solution, and the reaction product was extracted. After concentration of the organic layer, the product was purified by column chromatography to give 7 g of a compound (A-1).

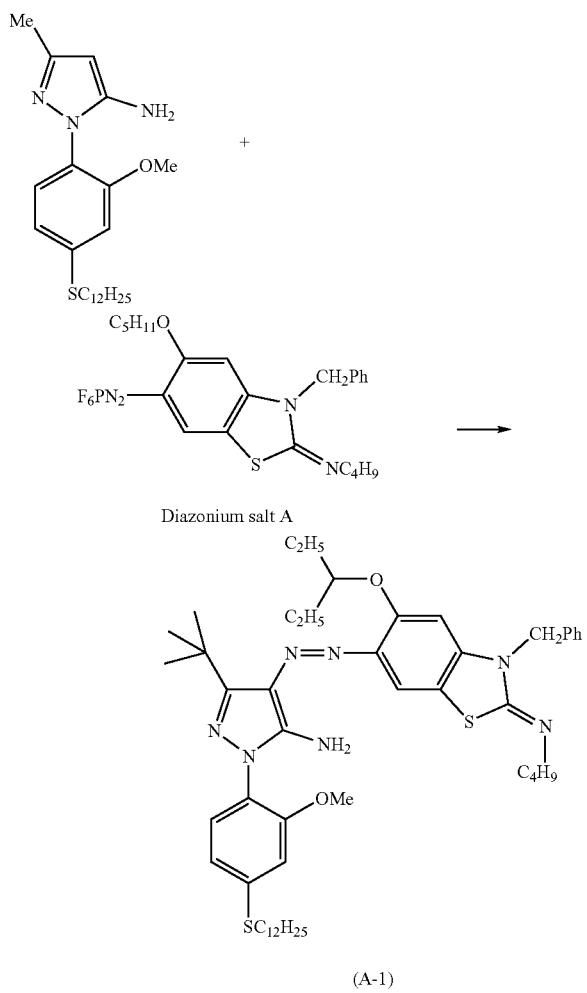

(A-1)

The $^1$H-NMR data of the compound (A-1) obtained were:
$^1$H-NMR (300 MHz, CDCl$_3$): δ0.8–1.8 (m, 49H), 3.3 (t, 2H), 3.80 (s, 3H), 3.85 (t, 2H), 3.9 (q, 1H), 5.2 (s, 2H), 6.4 (s, 1H), 6.6 (brs, 2H), 6.8 (d, 1H), 7.1 (s, 1H), 7.2–7.4 (m, 5H), 7.7 (s, 1H)

20

Example 2

<Synthesis of Compound (A-2)>

A compound (A-2) was synthesized in a similar manner to Example 1, except that the following coupler B was used replacing the coupler A. The $^1$H-NMR data of the compound (A-2) obtained were as follows:
$^1$H-NMR (300 MHz, CDCl$_3$): δ0.8–1.0 (m, 9H), 1.4–1.8 (m, 15H), 2.4 (s, 3H), 3.3 (t, 2H), 4.0 (q, 1H), 5.2 (s, 2H), 6.3 (s, 1H), 7.2–7.5 (m, 7H), 7.6 (s, 1H), 7.8 (d, 1H)

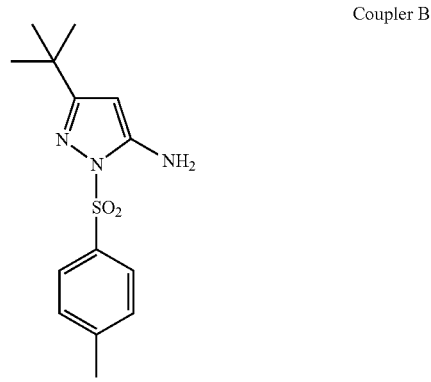

Coupler B

Example 3

<Synthesis of Compound (A-4)>

A compound (A-4) was synthesized in a similar manner to Example 1, except that the following coupler C was used replacing the coupler A. The $^1$H-NMR data of the compound (A-4) obtained were as follows:
$^1$H-NMR (300 MHz, CDCl$_3$): δ0.8–1.0 (m, 9H) 1.2–1.6 (m, 8H), 2.4 (s, 3H), 3.2 (t, 2H), 4.0 (q, 1H), 5.2 (s, 2H), 6.8 (s, 1H), 7.0 (d, 1H), 7.2–7.8 (m, 16H), 8.8 (s, 1H), 9.2 (s, 1H)

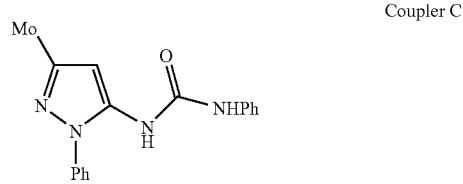

Coupler C

Example 4

<Synthesis of Compound (A-5)>

A compound (A-5) was synthesized in a similar manner to Example 1, except that the following coupler D was used replacing the coupler A. The $^1$H-NMR data of the compound (A-5) obtained were as follows:
$^1$H-NMR (300 MHz, CDCl$_3$): δ0.8–1.0 (m, 9H), 1.4–1.8 (m, 17H), 3.3 (t, 2H), 4.0 (q, 1H), 5.2 (s, 2H), 6.3 (s, 1H), 7.2 (t, 1H), 7.3–7.4 (m, 6H), 7.6 (m, 2H), 7.7 (s, 1H), 9.0 (s, 1H)

Example 5

\<Synthesis of Compound (A-10)\>

A compound (A-10) was synthesized in a similar manner to Example 1, except that the following coupler E was used replacing the coupler A. The ¹H-NMR data of the compound (A-10) obtained were as follows:

¹H-NMR (300 MHz, CDCl₃): δ0.8–1.0 (m, 9H), 1.4 (m, 2H), 1.6–1.8 (m, 13H), 3.3 (t, 2H), 4.1 (q, 1H), 5.2 (s, 2H), 6.3 (s, 1H), 7.2–7.4 (7H), 7.6 (m, 2H), 7.7 (s, 1H), 8.4 (brs, 2H)

Example 6

\<Synthesis of Compound (A-26)\>

A compound (A-26) was synthesized in a similar manner to Example 1, except that the following coupler F was used replacing the coupler A. The ¹H-NMR data of the compound (A-26) obtained were as follows:

¹H-NMR (300 MHz, CDCl₃): δ0.8–1.0 (m, 6H), 1.4–1.8 (m, 13H), 3.3 (t, 2H), 4.0 (m, 7H), 5.2 (s, 2H), 6.4 (s, 1H), 6.4 (s, 1H), 7.2–7.4 (m, 5H), 7.7 (s, 1H)

Example 7

\<Synthesis of Compound (A-27)\>

A compound (A-27) was synthesized in a similar manner to Example 1, except that the following coupler G was used replacing the coupler A. The ¹H-NMR data of the compound (A-27) obtained were as follows:

¹H-NMR (300 MHz, CDCl₃): δ0.8–1.0 (m, 6H), 1.4–1.7 (m, 13H), 3.3 (t, 2H), 4.0 (m, 7H), 5.1 (s, 2H), 5.9 (s, 1H), 6.4 (s, 1H), 7.2–7.4 (m, 5H), 7.8 (s, 1H)

Example 8

\<Synthesis of Compound (A-18)\>

A compound (A-18) was synthesized in a similar manner to Example 1, except that the following compounds (coupler H and diazonium salt B) were used as the coupler and diazonium salt. The ¹H-NMR data of the compound (A-18) obtained were as follows:

¹H-NMR (300 MHz, CDCl₃): □0.8–1.0 (m, 9H), 1.2–1.8 (m, 37H), 2.4 (s, 3H), 2.9 (t, 2H), 3.8 (t, 2H), 3.9 (s, 3H), 4.1 (t, 2H), 6.4 (s, 2H), 6.7 (s, 1H), 7.0 (s, 1H), 7.1 (d, 2H), 7.2 (d, 2H), 7.3–7.5 (m, 3H)

-continued

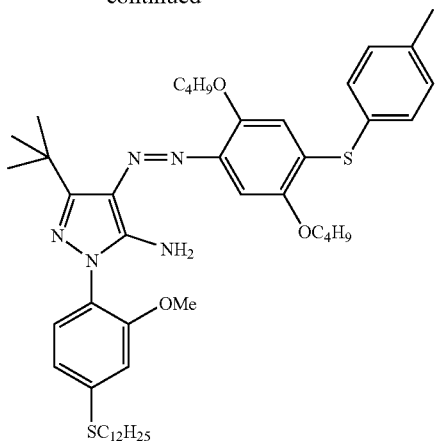

(A-18)

Comparative Example 1

The evaluations which will be explained later were performed by using the following comparative compound 1.

Comparative compound 1

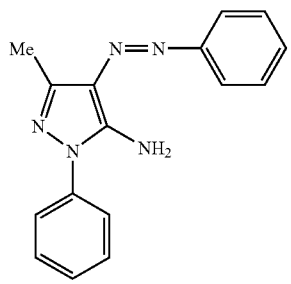

Comparative Example 2

The evaluations which will be explained later were performed by using the following comparative compound 2.

Comparative compound 2

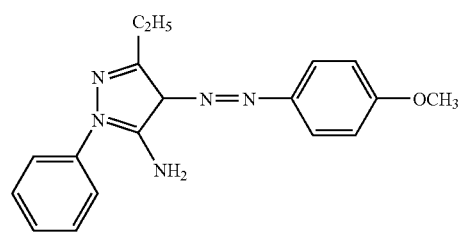

Evaluation

—Ultraviolet and Infrared Absorption Spectra—

The ultraviolet and infrared absorption spectra of each of the azo compounds of Examples 1 to 8 and Comparative Examples 1 to 2 were determined by preparing a solution of the compound in a chloroform/methanol (=1/1) mixture ($2.0 \times 10^{-5}$ M) and placing it in a quartz cell of 1 cm square and using an spectrophotometer MPS-2400 (manufactured by Shimadzu Corporation). The maximum absorption wavelengths and the molar extinction coefficients of respective azo compounds are summarized in Table 1.

—Light Fastness in Solution—

A solution of each of the azo compounds of Examples 1 to 8 and Comparative Examples 1 and 2 in butyl acetate ($2.0 \times 10^{-5}$ M) was placed in a quartz cell of 1 cm square and irradiated with a xenon light for 24 hours by using a merry-go-round light fastness tester (manufactured by Eagle Engineering) equipped with a 500-W xenon light lamp. The residual ratio of each azo compound after the xenon light irradiation was calculated by the change in ultraviolet and infrared absorption spectrum. The residual ratios are summarized in Table 1.

TABLE 1

| | Azo compound | Maximum absorption wavelength (nm) | Molar extinction coefficient | Residual ratio in light fastness test (%) |
|---|---|---|---|---|
| Example 1 | Compound (A-1) | 446 | 33000 | 82 |
| Example 2 | Compound (A-2) | 449 | 30300 | 75 |
| Example 3 | Compound (A-4) | 447 | 31000 | 73 |
| Example 4 | Compound (A-5) | 448 | 31200 | 71 |
| Example 5 | Compound (A-10) | 450 | 34700 | 81 |
| Example 6 | Compound (A-26) | 450 | 32300 | 70 |
| Example 7 | Compound (A-27) | 449 | 33200 | 72 |
| Example 8 | Compound (A-18) | 445 | 32300 | 80 |
| Comparative Example 1 | Comparative compound 1 | 369 | 25000 | 56 |
| Comparative Example 2 | Comparative compound 2 | 428 | 29000 | 65 |

As apparent from Table 1, the azo compounds of Examples 1 to 8 had a hue favorable for use as a dye and were especially superior in light fastness, compared to those of Comparative Examples 1 and 2.

Thus, the invention provides a new azo compound and the tautomer thereof and an azo dye that are favorable in hue and superior in light fastness.

What is claimed is:

1. An azo compound or the tautomer thereof represented by the following Formula (1-1):

Formula (1-1)

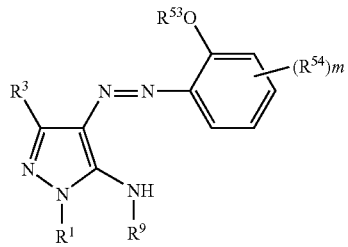

wherein, $R^1$ represents a hydrogen atom, alkyl group, aryl group, acyl group, carbamoyl group, alkylsulfonyl group, arylsulfonyl group, or heterocyclic group; $R^3$ represents a hydrogen atom, alkyl group, aryl group, alkoxy group aryloxy group, acylamino group, carbamoylamino group, alkylsulfonylamino group, or arylsulfonylamino group; $R^9$ represents a hydrogen atom, alkyl group, aryl group, acyl group, carbamoyl group, alkylsulfonyl group, or arylsulfonyl group; $R^{53}$ represents an alkyl group or aryl group; m is an integer of 2 to 4; and each $R^{54}$, of which there are m in number, independently represents an alkyl group, aryl group, alkoxy group, aryloxy group, amino group, alkylthio group, arylthio group, acylamino group, alkylsulfonylamino group, or arylsulfonylamino group, and one $R^{54}$ bind to another $R^{54}$ forming a ring.

2. The azo compound or the tautomer thereof according to claim 1, wherein m in Formula (1-1) is 2.

3. An azo compound or the tautomer thereof represented by the following Formula (2):

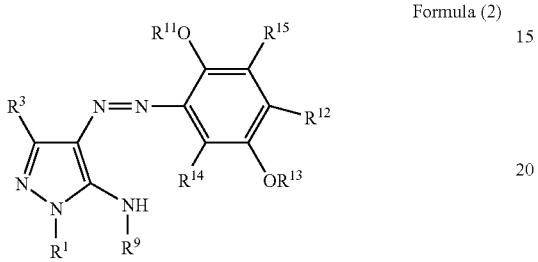

Formula (2)

wherein, $R^1$ represents a hydrogen atom, alkyl group, aryl group, acyl group, carbamoyl group, alkylsulfonyl group, arylsulfonyl group, or heterocyclic group; $R^9$ represents a hydrogen atom, alkyl group, aryl group, acyl group, carbamoyl group, alkylsulfonyl group, or arylsulfonyl group; $R^3$ represents a hydrogen atom, alkyl group, aryl group, alkoxy group, aryloxy group, acylamino group, carbamoylamino group, alkylsulfonylamino group, or arylsulfonylamino group; $R^{11}$ and $R^{13}$ each independently represent an alkyl group or aryl group; $R^{12}$ represents an alkoxy group, aryloxy group, amino group, alkylthio group, arylthio group, acylamino group, alkylsulfonylamino group or arylsulfonylamino group; and $R^{14}$ and $R^{15}$ each independently represent a hydrogen atom, alkyl group, alkoxy group, or aryloxy group.

4. An azo compound or the tautomer thereof represented by the following Formula (3):

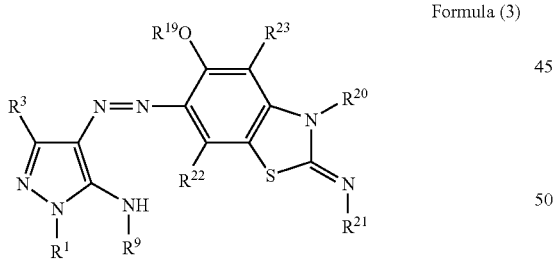

Formula (3)

wherein, $R^1$ represents a hydrogen atom, alkyl group, aryl group, acyl group, carbamoyl group, alkylsulfonyl group, arylsulfonyl group, or heterocyclic group; $R^9$ represents a hydrogen atom, alkyl group, aryl group, acyl group, carbamoyl group, alkylsulfonyl group, or arylsulfonyl group; $R^3$ represents a hydrogen atom, alkyl group, aryl group, alkoxy group, aryloxy group, acylamino group, carbamoylamino group, alkylsulfonylamino group, or arylsulfonylamino group; $R^{19}$ represents an alkyl group or aryl group; $R^{20}$ represents a hydrogen atom, alkyl group, or aryl group; $R^{21}$ represents a hydrogen atom, alkyl group, aryl group, acyl group, alkylsulfonyl group, arylsulfonyl group, or carbamoyl group; and $R^{22}$ and $R^{23}$ each independently represent a hydrogen atom, alkyl group, or aryl group.

5. A dye composition including an azo compound wherein the azo compound is represented by the following Formula (1-1):

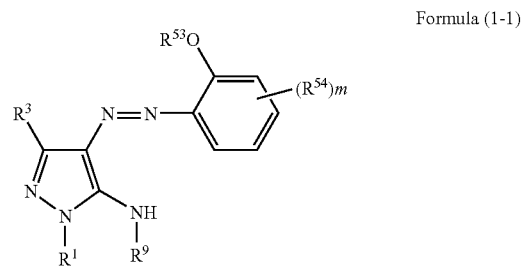

Formula (1-1)

wherein, $R^1$ represents a hydrogen atom, alkyl group, aryl group, acyl group carbamoyl group, alkylsulfonyl group, arylsulfonyl group, or heterocyclic group; $R^3$ represents a hydrogen atom, alkyl group, aryl group, alkoxy group, aryloxy group, acylamino group, carbamoylamino group, alkylsulfonylamino group, or arylsulfonylamino group; $R^9$ represents a hydrogen atom, alkyl group, aryl group, acyl group carbamoyl group, alkylsulfonyl group, or arylsulfonyl group; $R^{53}$ represents an alkyl group or aryl group; m is an integer of 2 to 4; and each $R^{54}$, of which there are m in number, independently represents an alkyl group, aryl group, alkoxy group, aryloxy group, amino group, alkylthio group, arylthio group, acylamino group, alkylsulfonylamino group, or arylsulfonylamino group, and one may bind to another $R^{54}$ forming a ring.

6. The dye composition according to claim 5, wherein m in the Formula (1-1) is 2.

7. A dye composition including an azo compound wherein the azo compound is represented by the following Formula (2):

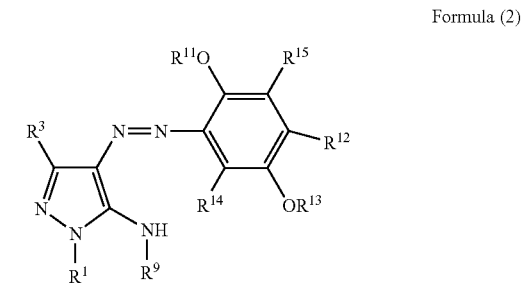

Formula (2)

wherein, $R^1$ represents a hydrogen atom, alkyl group, aryl group, acyl group, carbamoyl group, alkylsulfonyl group, arylsulfonyl group, or heterocyclic group; $R^9$ represents a hydrogen atom, alkyl group, aryl group, acyl group, carbamoyl group, alkylsulfonyl group, or arylsulfonyl group; $R^3$ represents a hydrogen atom, alkyl group, aryl group, alkoxy group, aryloxy group, acylamino group, carbamoylamino group, alkylsulfonylamino group, or arylsulfonylamino group; $R^{11}$ and $R^{13}$ each independently represent an alkyl group or aryl group; $R^{12}$ represents an alkoxy group, aryloxy group, amino group, alkylthio group, arylthio group, acylamino group, alkylsulfonylamino group, or arylsulfonylamino group; and $R^{14}$ and $R^{15}$ each independently represent a hydrogen atom, alkyl group, alkoxy group, or aryloxy group.

8. A dye composition including an azo compound wherein the azo compound is represented by the following Formula (3):

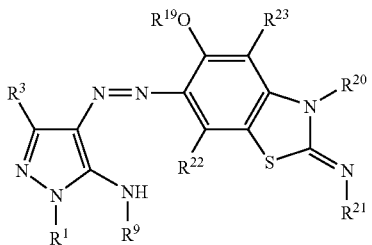

Formula (3)

wherein, $R^1$ represents a hydrogen atom, alkyl group, aryl group, acyl group, carbamoyl group, alkylsulfonyl group, arylsulfonyl group, or heterocyclic group; $R^9$ represents a hydrogen atom, alkyl group, aryl group, acyl group, carbamoyl group, alkylsulfonyl group, or arylsulfonyl group; $R^3$ represents a hydrogen atom, alkyl group, aryl group, alkoxy group, aryloxy group, acylamino group, carbamoylamino group, alkylsulfonylamino group, or arylsulfonylamino group; $R^{19}$ represents an alkyl group or aryl group; $R^{20}$ represents a hydrogen atom, alkyl group, or aryl group; $R^{21}$ represents a hydrogen atom, alkyl group, aryl group, acyl group, alkylsulfonyl group, arylsulfonyl group, or carbamoyl group; and $R^{22}$ and $R^{23}$ each independently represent a hydrogen atom, alkyl group, or aryl group.

* * * * *